United States Patent
Meyers et al.

(10) Patent No.: US 6,719,800 B2
(45) Date of Patent: Apr. 13, 2004

(54) CONSTRAINED PROSTHETIC KNEE WITH ROTATING BEARING

(75) Inventors: John E. Meyers, Columbia City, IN (US); G. Doug Letson, Tampa, FL (US); Russell Windsor, Larchmont, NY (US); Vincent A. Webster, Warsaw, IN (US); Bill N. Sisk, Claypool, IN (US); Bill H. Haywood, Warsaw, IN (US); Adam Griner, Columbia City, IN (US); Michael Cook, Silver Lake, IN (US); Rodney L. Bays, Pierceton, IN (US); Jerry L. Aikins, Warsaw, IN (US); Marvin Figueroa, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 58 days.

(21) Appl. No.: 10/001,000

(22) Filed: Nov. 2, 2001

(65) Prior Publication Data

US 2002/0107576 A1 Aug. 8, 2002

Related U.S. Application Data

(63) Continuation-in-part of application No. 09/771,061, filed on Jan. 29, 2001, now Pat. No. 6,485,519.

(51) Int. Cl.[7] .................................................. A61F 2/38
(52) U.S. Cl. ................................. 623/20.24; 623/18.11
(58) Field of Search ........................... 623/20.14–20.34, 623/18.11

(56) References Cited

U.S. PATENT DOCUMENTS

| 3,696,446 A | 10/1972 | Bousquet et al. |
| 3,813,700 A | 6/1974 | Tavernetti et al. |
| 3,824,630 A | 7/1974 | Johnston |

(List continued on next page.)

FOREIGN PATENT DOCUMENTS

| CA | 1073151 | 3/1980 |
| DE | 2 122 390 | 1/1973 |
| EP | 0 046 926 | 8/1981 |
| EP | 0 069 683 A1 | 6/1982 |
| EP | 0 083 155 A1 | 11/1982 |
| EP | 0 126 978 | 4/1984 |
| EP | 0 194 326 A1 | 3/1985 |
| EP | 0 177 755 A1 | 9/1985 |
| EP | 0 178 445 A1 | 9/1985 |
| EP | 0 198 163 A2 | 2/1986 |
| EP | 0 265 325 | 4/1988 |
| EP | 0 410 237 A1 | 1/1990 |
| EP | 0 420 460 A1 | 4/1991 |
| EP | 0 472 475 A2 | 2/1992 |
| GB | 2 129 306 | 5/1984 |
| WO | WO 94/21198 | 9/1994 |

*Primary Examiner*—Kevin Shaver
*Assistant Examiner*—Michael B. Priddy
(74) *Attorney, Agent, or Firm*—Baker & Daniels

(57) ABSTRACT

A constrained prosthetic knee having a modular hinge post and a rotating bearing. A cannulated hinge post is rotatably connected to the femoral component of the knee prosthesis so that a hinge post extension may be anteriorly positioned through the hinge post and into the tibial component of the knee prosthesis, after positioning of the femoral component in the femur and the tibial component in the tibia. The hinge post is preassembled to the femoral component so that such assembly is not required during the implantation procedure. A meniscal component forming the rotating bearing of the knee prosthesis is packaged together with the hinge post extension so that the appropriate hinge post extension is readily available. The meniscal component includes a mechanism for preventing lift off of the meniscal component from the tibial component, while allowing rotation of the meniscal component relative to the tibial component.

25 Claims, 12 Drawing Sheets

U.S. PATENT DOCUMENTS

| | | | |
|---|---|---|---|
| 3,869,729 A | | 3/1975 | Attenborough |
| 3,918,101 A | | 11/1975 | LaGrange et al. |
| 3,934,272 A | | 1/1976 | Wearne et al. |
| 3,996,624 A | | 12/1976 | Noiles |
| 4,016,606 A | | 4/1977 | Murray et al. |
| 4,112,522 A | | 9/1978 | Dadurian et al. |
| 4,134,158 A | | 1/1979 | Laure |
| 4,136,405 A | * | 1/1979 | Pastrick et al. ........... 623/20.25 |
| 4,219,893 A | | 9/1980 | Noiles |
| 4,224,697 A | | 9/1980 | Murray |
| 4,262,368 A | | 4/1981 | Lacey |
| 4,301,553 A | * | 11/1981 | Noiles ...................... 623/20.25 |
| 4,340,978 A | | 7/1982 | Buechel et al. |
| 4,358,859 A | | 11/1982 | Schurman et al. |
| 4,462,120 A | | 7/1984 | Rambert et al. |
| 4,662,889 A | | 5/1987 | Zichner et al. |
| 4,790,853 A | | 12/1988 | Engelbrecht et al. |
| 4,822,366 A | | 4/1989 | Bolesky |
| 4,828,564 A | | 5/1989 | Scales et al. |
| 4,834,758 A | | 5/1989 | Lane et al. |
| 4,865,606 A | | 9/1989 | Rehder |
| 4,888,021 A | | 12/1989 | Forte et al. |
| 4,919,660 A | | 4/1990 | Peilloud |
| 4,923,472 A | | 5/1990 | Ugolini |
| 4,936,853 A | | 6/1990 | Fabian et al. |
| 4,938,769 A | | 7/1990 | Shaw |
| 5,007,933 A | | 4/1991 | Sidebotham et al. |
| 5,011,496 A | | 4/1991 | Forte et al. |
| 5,019,103 A | | 5/1991 | Van Zile et al. |
| 5,037,439 A | | 8/1991 | Albrektsson et al. |
| 5,116,375 A | | 5/1992 | Hoffman |
| 5,123,928 A | | 6/1992 | Moser |
| 5,139,521 A | | 8/1992 | Schelhas |
| 5,180,383 A | | 1/1993 | Haydon |
| 5,194,066 A | | 3/1993 | Van Zile |
| 5,246,459 A | * | 9/1993 | Elias ........................ 623/20.34 |
| 5,282,867 A | | 2/1994 | Mikhail |
| 5,314,481 A | | 5/1994 | Bianco |
| 5,358,527 A | | 10/1994 | Forte |
| 5,370,701 A | * | 12/1994 | Finn ........................ 623/20.25 |
| 5,405,398 A | | 4/1995 | Buford, III et al. |
| 5,411,555 A | | 5/1995 | Nieder |
| 5,413,607 A | | 5/1995 | Engelbrecht et al. |
| 5,458,644 A | | 10/1995 | Grundei |
| 5,489,311 A | | 2/1996 | Cipolletti |
| 5,549,687 A | | 8/1996 | Coates et al. |
| 5,549,689 A | | 8/1996 | Epstein et al. |
| 5,755,804 A | | 5/1998 | Schmotzer et al. |
| 5,800,552 A | | 9/1998 | Forte |
| 5,824,096 A | | 10/1998 | Pappas et al. |
| 5,879,392 A | | 3/1999 | McMinn |
| 5,954,770 A | | 9/1999 | Schmotzer et al. |
| 6,004,352 A | * | 12/1999 | Buni ........................ 623/20.33 |
| 6,019,794 A | | 2/2000 | Walker |
| 6,099,570 A | | 8/2000 | Livet et al. |
| 6,143,034 A | | 11/2000 | Burrows |
| 6,306,172 B1 | * | 10/2001 | O'Neil et al. ............. 623/20.15 |
| 2002/0161448 A1 | * | 10/2002 | Hayes et al. .............. 623/20.32 |

* cited by examiner

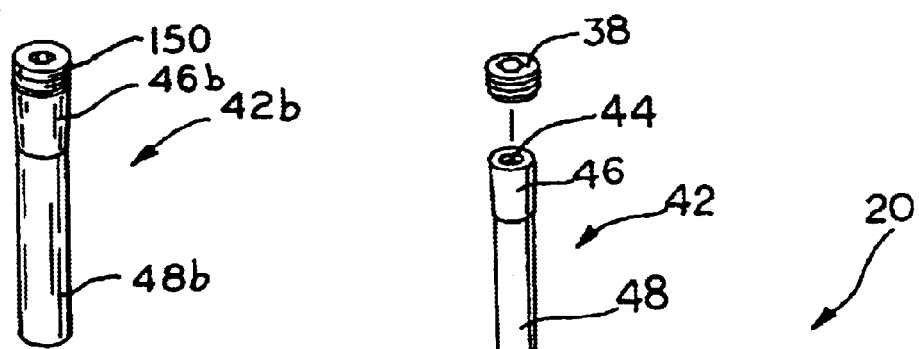
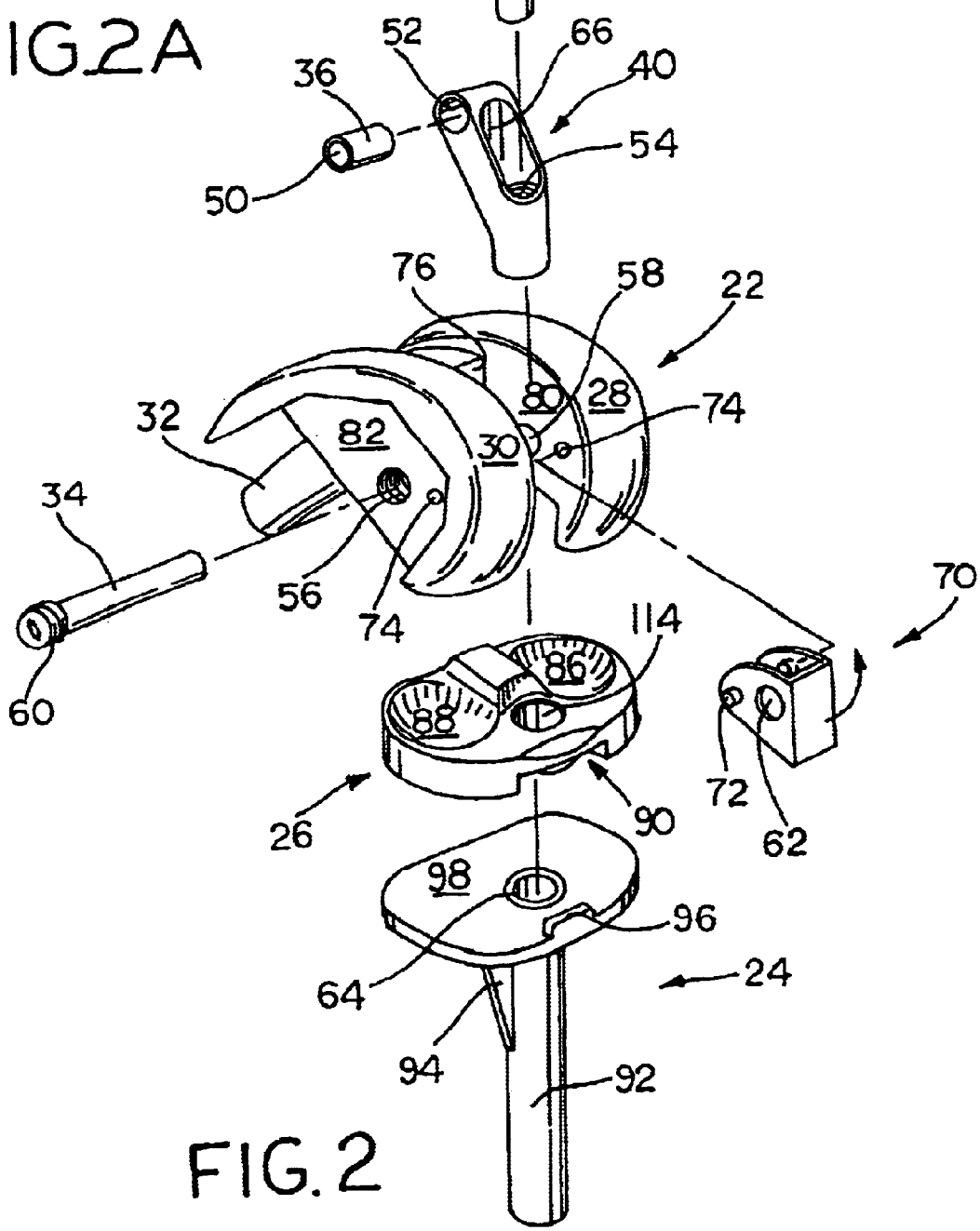

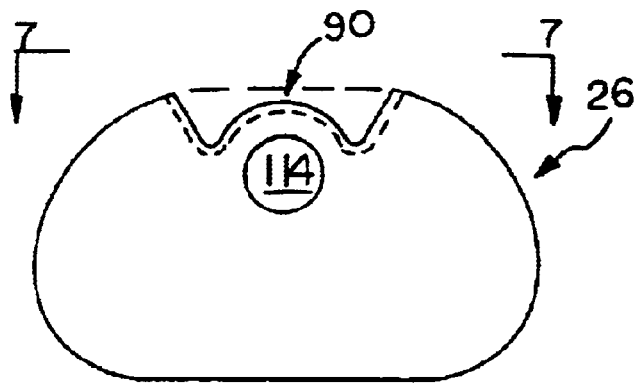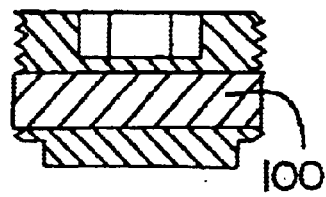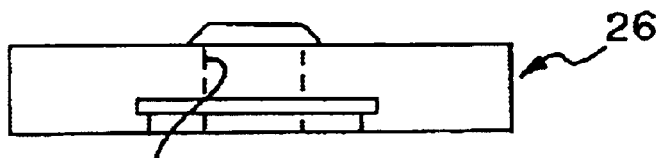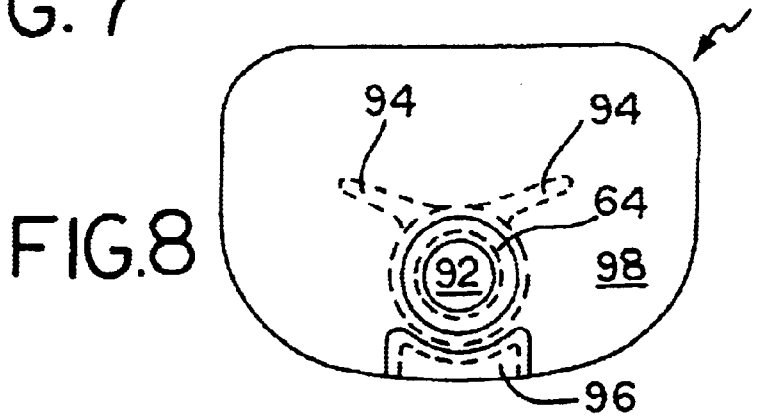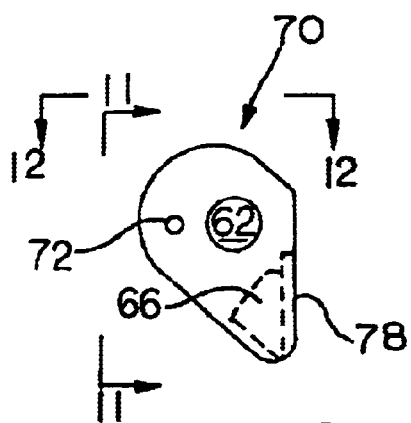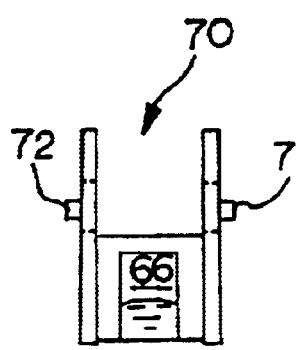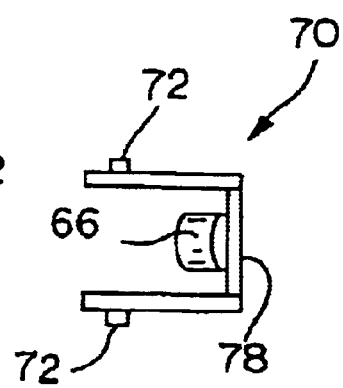

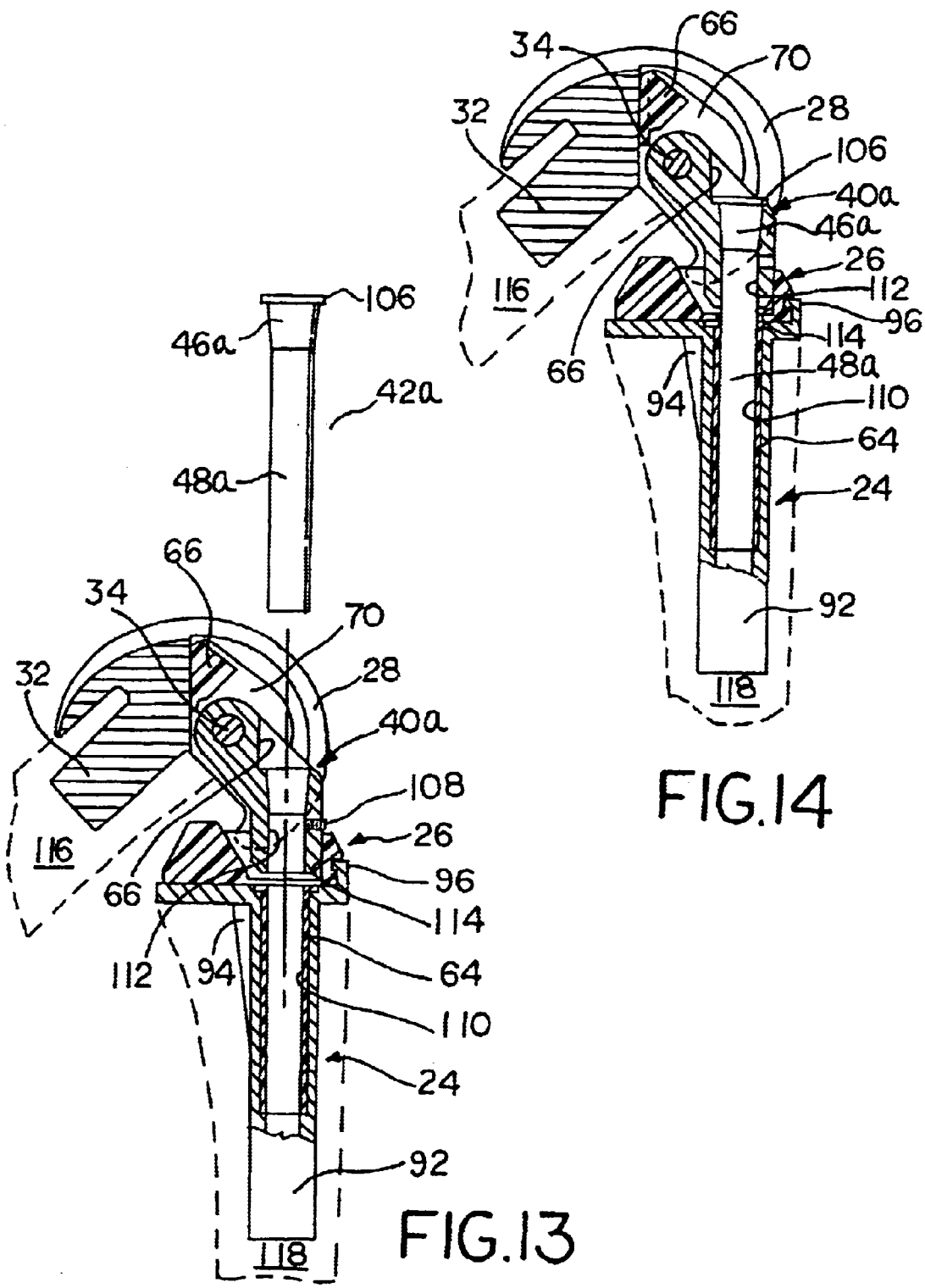

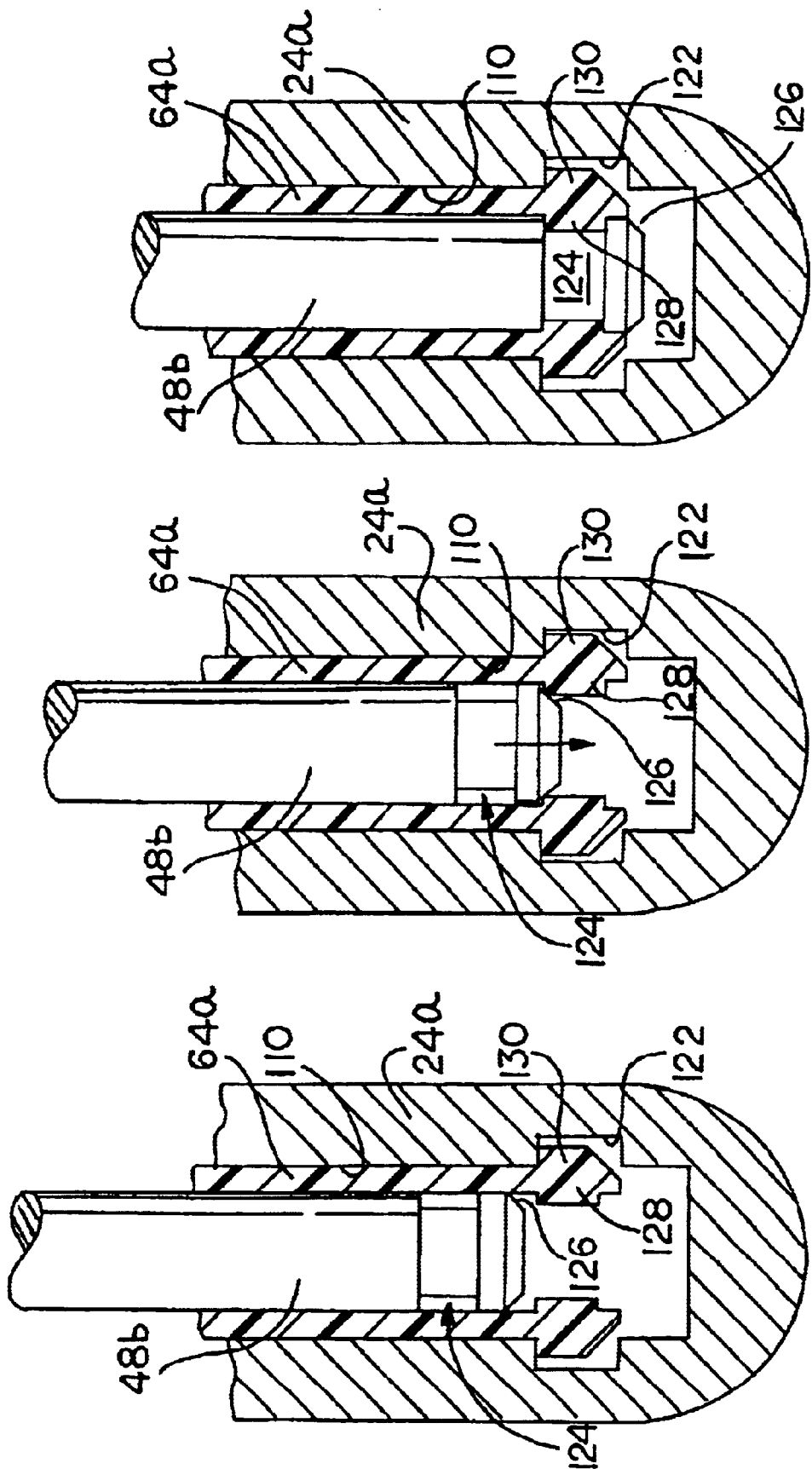

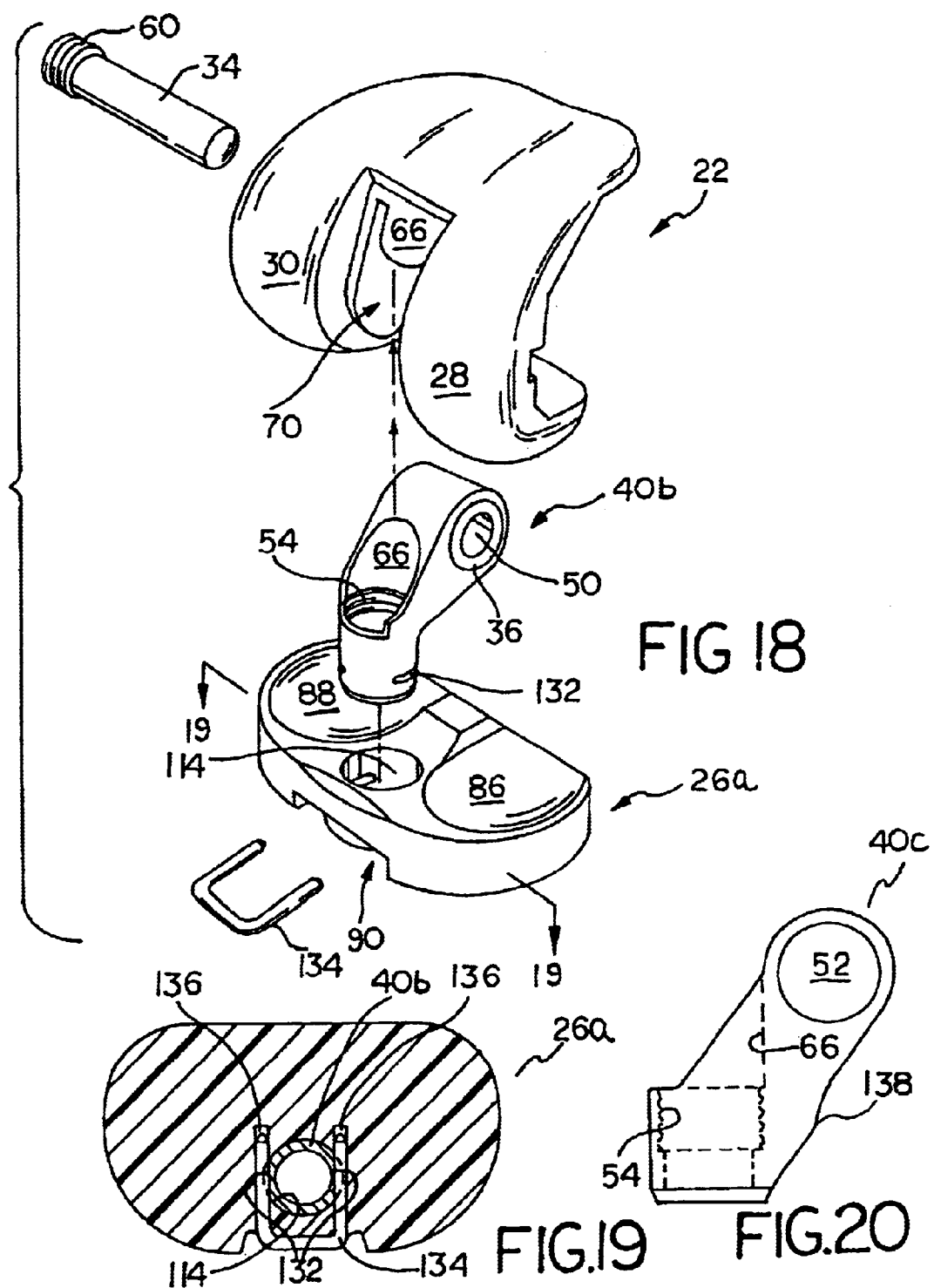

CONSTRAINED PROSTHETIC KNEE WITH ROTATING BEARING

CROSS-REFERENCE TO RELATED APPLICATION

This is a continuation-in-part of patent application Ser. No. 09/771,061, filed Jan. 29, 2001, now U.S. Pat. No. 6,485,519.

BACKGROUND OF THE INVENTION

1. Field of the Invention

The present invention relates to prosthetic joints, and, more particularly to a constrained prosthetic knee having a modular hinge post and a rotating bearing.

2. Description of the Related Art

Generally, the knee is formed by the pair of condyles at the distal portion of the femur, the lower surfaces of which bear upon the correspondingly shaped proximal surface plateau of the tibia. The femur and tibia are connected by means of ligaments such as, the posterior cruciate ligament, the lateral collateral ligament, the medial collateral ligament, and the anterior cruciate ligament. These ligaments provide stability to the joint formed by the femur and tibia (i.e., the knee).

In a broad sense, prosthetic knee joints can be considered either constrained or unconstrained. For the purposes of this discussion, constrained prosthetic knees include femoral and tibial prosthetic components which are mechanically linked or constrained to each other by a hinge structure. An unconstrained prosthetic knee includes femoral and tibial components which are not mechanically linked. An unconstrained knee utilizes the patient's existing ligaments to provide joint stability. With this in mind, constrained prosthetic knees have particular applicability to cases in which a patient has experienced ligament loss and/or the existing ligaments do not provide adequate support and stability to the knee.

Tibial components of a prosthetic knee can be formed as a one-piece configuration in which the tibial tray forms the meniscal component of the prosthetic knee. Various other prosthetic knees utilize a modular meniscal component separate from the tibial component. Devices utilizing modular meniscal components include those in which the meniscal component (i.e., tibial bearing surface) is fixed to the tibial tray portion of the tibial component and is incapable of movement relative thereto. Alternative devices utilize a modular meniscal component capable of movement relative to the tibial tray. Devices in which relative rotational movement occurs between the meniscal component and the tibial component are typically referred to as rotating bearing knees. Rotating bearing knees thus allow movement between the bearing (i.e., meniscal component) and the tibial tray, as well as movement between the femoral component and the tibial bearing.

Constrained knees of the prior art include constructions in which a hinge post extension is first positioned within a tibial component (with an end protruding therefrom) and is thereafter connected to the femoral component by positioning the hinge post (rotatably attached to the femoral component) over the top of the protruding end of the hinge post extension and thereafter connecting the hinge post extension to the hinge post, e.g., by threading the hinge post extension into the hinge post. After making this connection, the meniscal component is thereafter slid into position between the femoral component and the tibial component. Meniscal components utilized with these prior art prosthetic knees are fixed to the tibial component.

The present invention is directed to a constrained knee prosthesis with a rotating bearing. The knee prosthesis of the present invention is structured to facilitate implantation thereof. The present invention is further directed to a prosthetic knee implant set having a plurality of matched modular hinge post and meniscal component pairs.

SUMMARY OF THE INVENTION

The present invention provides an improved constrained knee prosthesis having a cannulated hinge post facilitating implantation of the knee prosthesis in a relatively minimally invasive procedure. The prosthetic knee implant set of the current invention includes a separately packaged femoral component, a separately packaged tibial component, and a third package containing a hinge post extension and the meniscal component. Packaging the individual components of a knee prosthesis in this fashion insures that the appropriate hinge post extension is readily available. A bearing box is interposed between the hinge post and the femoral component. The bearing box includes a hyperextension stop which cooperates with the hinge post to prevent hyperextension of the knee prosthesis. Various structures are utilized to prevent the disengagement of the constrained knee prosthesis of the present invention.

A prosthetic knee constructed in accordance with the present invention includes a femoral component having a pair of condyler surfaces and a hinge post rotatably connected to the femoral component between the condyler surfaces. The hinge post is cannulated and accommodates insertion of a hinge post extension shaft therein. The hinge post and hinge post extension include cooperating locking tapers for locking the hinge post extension to the hinge post. Additionally, the hinge post includes internal threads so that a set screw may be threaded therein to further hold the hinge post extension in place. In one exemplary embodiment, the proximal end of the hinge post extension is threaded to facilitate locking the hinge post extension to the hinge post. The tibial component includes a hinge post extension aperture into which the hinge post extension is seated. The meniscal component similarly includes an aperture to accommodate the hinge post and hinge post extension. The meniscal component of the current invention is free to rotate about the hinge post during flexion and extension of the knee joint.

Having a cannulated hinge post through which a hinge post extension may be anteriorly positioned and secured advantageously allows for a relatively minimally invasive knee replacement procedure.

The present invention advantageously provides a constrained prosthetic knee having a rotating bearing flush with the condyler surfaces of the femoral component.

Another advantage of the present invention is the packaging of the prosthesis components and specifically the packaging of the appropriate hinge post extension together with a meniscal component.

BRIEF DESCRIPTION OF THE DRAWINGS

The above-mentioned and other features and advantages of this invention, and the manner of attaining of them, will become more apparent and the invention itself will be better understood by reference to the following description of an embodiment of the invention taken in conjunction with the accompanying drawings, wherein:

FIG. 2 is an exploded view thereof;

FIG. 2A is a perspective view of a hinge post extension of the present invention;

FIG. 6 is a bottom elevational view of the meniscal component of the present invention;

FIG. 7 is a front elevational view thereof;

FIG. 8 is a top elevational view of a tibial component in accordance with the present invention;

FIG. 9 is a sectional view of a hinge plug in accordance with the present invention;

FIG. 10 is a side elevational view of a bearing box in accordance with the present invention;

FIG. 11 is a front elevational view thereof;

FIG. 12 is a top elevational view thereof;

FIG. 13 is a cutaway, exploded view of an alternative embodiment of the knee prosthesis of the present invention;

FIG. 14 is a cutaway view of an assembled knee prosthesis in accordance with the embodiment illustrated in FIG. 13;

FIG. 15 is a fragmentary, cutaway view of an alternative embodiment of the hinge post extension and tibial bushing of the present invention;

FIG. 16 is a fragmentary, cutaway view of the embodiment of FIG. 15 illustrating insertion of the hinge post extension into the tibial bushing;

FIG. 17 is a fragmentary, cutaway view of the embodiment of FIG. 15 illustrating the hinge post extension fully inserted into the tibial bushing;

FIG. 18 is an exploded view of an alternative embodiment of the knee prosthesis of the current invention;

FIG. 19 is a sectional view of a meniscal component in accordance with an alternative embodiment of the present invention;

FIG. 20 is an elevational view of a hinge post in accordance with an alternative embodiment of the present invention;

Figure 1:
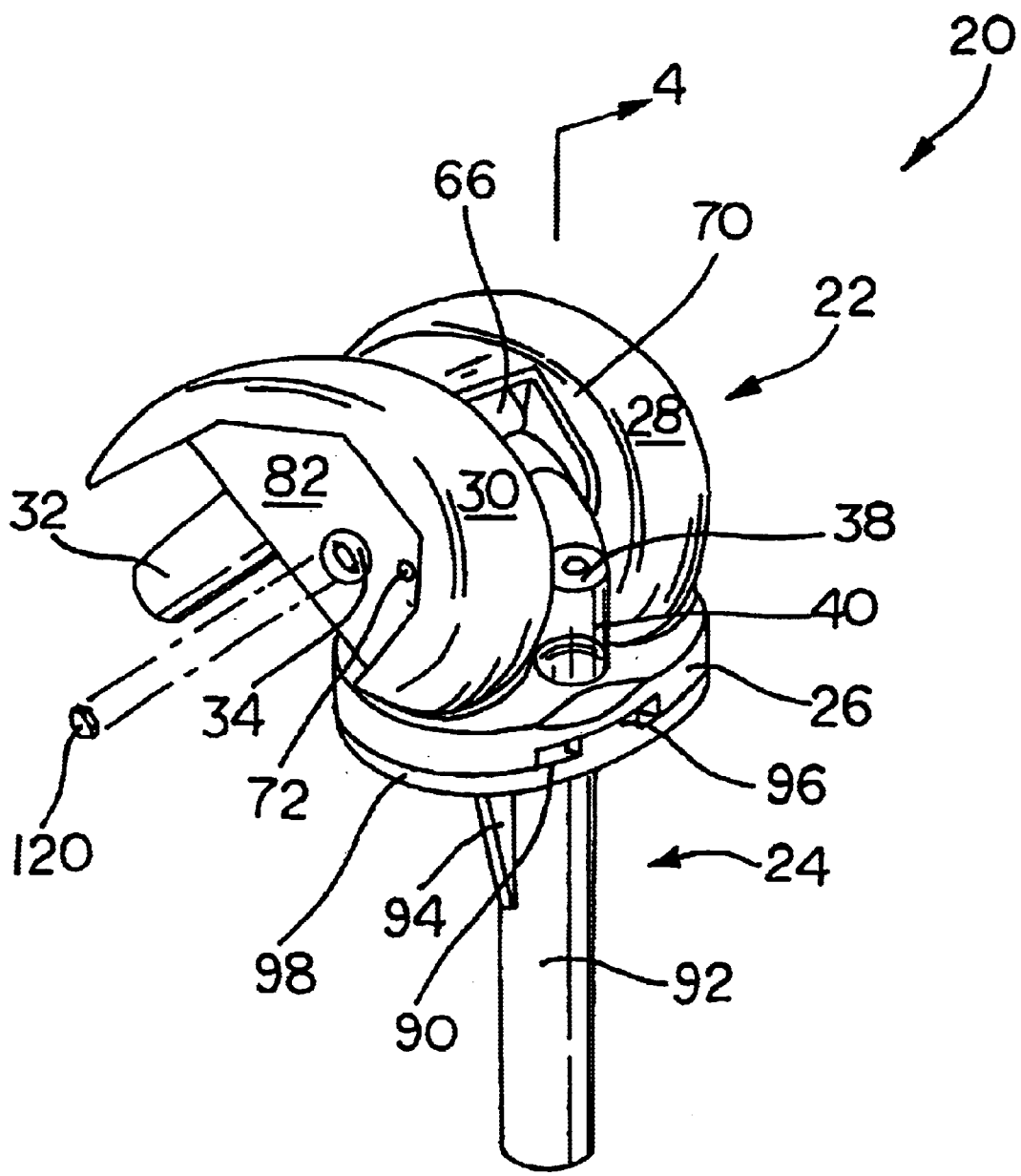
FIG. 1 is a perspective view of an assembled knee prosthesis in accordance with the present invention.
Figure 3:
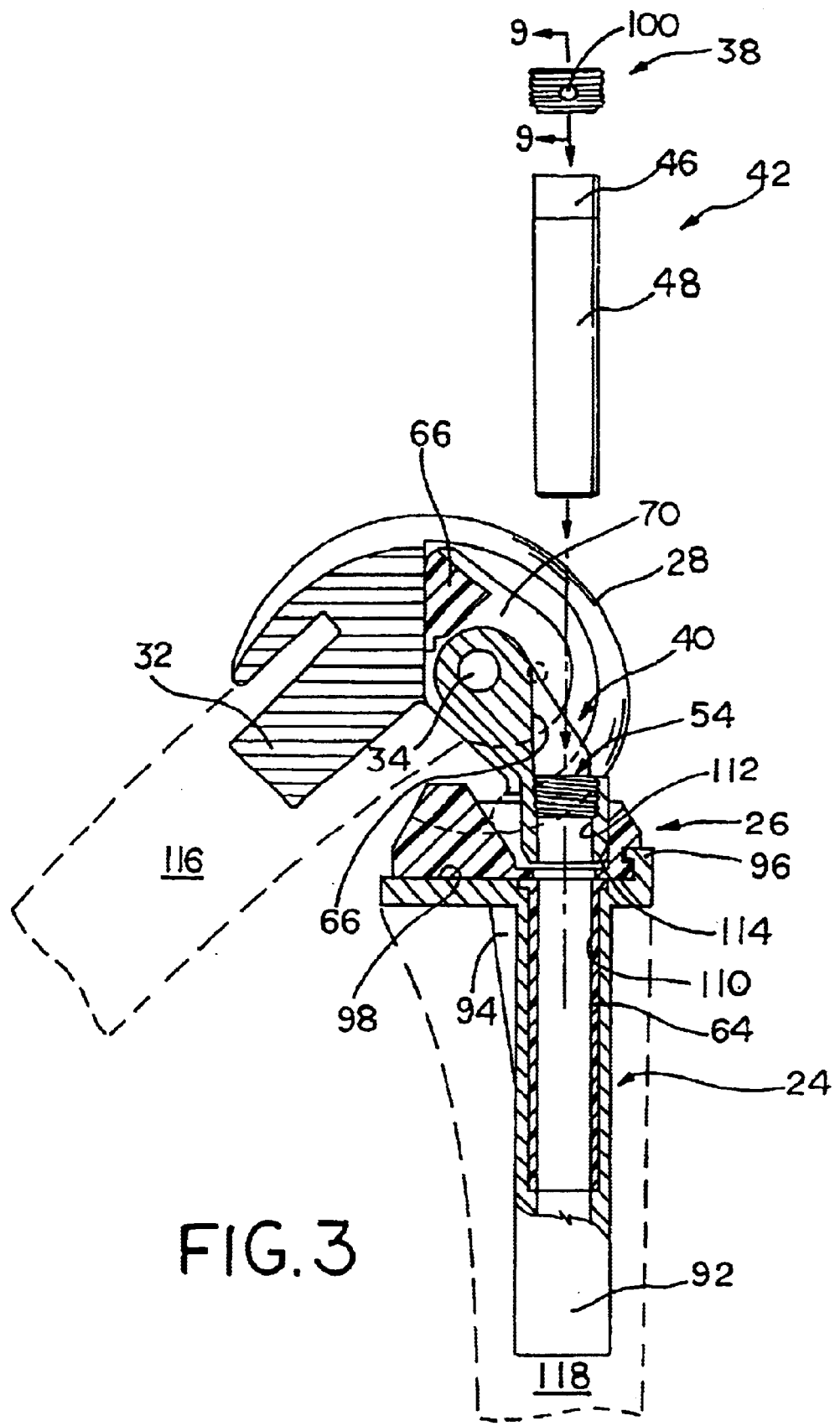
FIG. 3 is a cutaway, exploded view illustrating assembly of the knee prosthesis of the current invention including the anterior positioning of the hinge post extension into the hinge post.

Corresponding reference characters indicate corresponding parts throughout the several views. Although the drawings represent embodiments of the invention, the drawings are not necessarily to scale and certain features may be exaggerated to better illustrate and explain the invention. The exemplifications set out herein illustrate embodiments of the invention, in alternative forms, and such exemplifications are not to be construed as limiting the scope of the invention in any manner.

DETAILED DESCRIPTION

Referring now to the drawings and particularly to FIG. 2, knee prosthesis 20 in accordance with the present invention is illustrated. Knee prosthesis 20 generally includes femoral component 22, tibial component 24, and meniscal component 26. Hinge post 40 is rotatably connected to femoral component 22 and includes elongate hinge post extension aperture 112 (FIGS. 3–6, 13, and 14). Elongate aperture 112 accommodates placement of hinge post extension 42 therein. Hinge post extension 42 thereafter traverses hinge post aperture 114 in meniscal component 26 and hinge post extension aperture 110 (FIGS. 3–6, 13 and 14) in tibial component 24. Elongate hinge post extension aperture 112 of hinge post 40 advantageously allows for anterior placement of hinge post extension 42 during surgical implantation of knee prosthesis 20 of the present invention.

Figure 4:
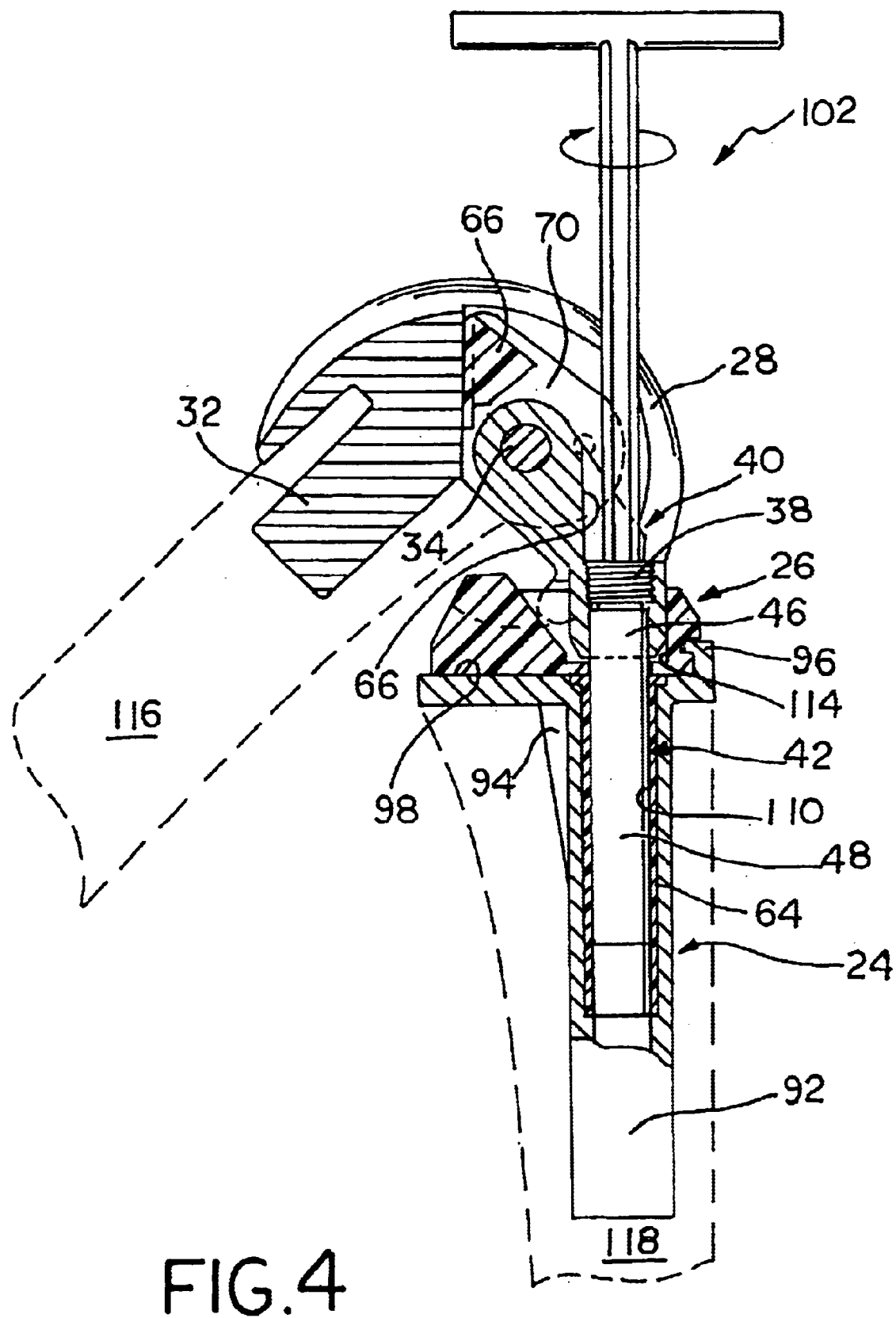
FIG. 4 is a cutaway view illustrating securement of the hinge plug (i.e., set screw) in the hinge post to facilitate locking of the hinge post extension therein.

As illustrated in FIG. 2, hinge post extension 42 includes locking taper 46 and cylindrical extension 48. Hinge post extension aperture 112 includes a mating locking taper to cooperate with locking taper 46 and lock hinge post extension 42 to hinge post 40. After positioning of hinge post extension 42 through apertures 112, 114, and 110, hinge plug 38 may be threaded into hinge plug threads 54 in elongate aperture 112 of hinge post 40 (FIG. 4). Hinge plug 38 abuts the end of hinge post extension 42 and thereby facilitates locking of morse taper 46 in elongate aperture 112. In one exemplary embodiment, locking taper 46 comprises a two degree locking taper. In an alternative embodiment, the hinge post extension includes integral threads to facilitate locking of the hinge post extension to the hinge post. As illustrated in FIG. 2A, hinge post extension 42b includes locking taper 46b as well as threaded proximal end 150. If hinge post extension 42b is utilized, hinge plug 38 is unnecessary. When prosthetic knee 20 is assembled as illustrated in FIG. 1, condyler bearing surfaces 28, 30 abut bearing surfaces 86, 88 (see, e.g., FIG. 2) in meniscal component 26.

Hinge post extension 42 is typically formed as a one-piece construction of an inert metal such as e.g., a cobalt-chromium alloy. Hinge post extension 42 may, however, be constructed of other bio-compatible metals or alloys, such as titanium. Throughout this document reference will be made to various components formed of a cobalt-chromium alloy. Any such component may also be constructed of other bio-compatible metals or alloys such as titanium, as is well-known. As illustrated in FIG. 4, hinge plug wrench 102 is utilized to thread hinge plug 38 into hinge plug threads 54 of hinge post 40. As illustrated in FIG. 9, hinge plug 38 includes locking material 100 to provide a locking connection between hinge plug 38 and hinge plug threads 54 in hinge post 40. Hinge plug 38 is, in one exemplary embodiment formed of a cobalt-chromium alloy. Locking material 100 comprises any suitable biocompatible polymer such as, e.g., ultra-high molecular weight polyethylene (UHMWPE).

As illustrated, e.g., in FIG. 2, femoral component 22 includes condyler bearing surfaces 28, 30 with bearing box wall 76 positioned therebetween. Femoral component 22 further includes external side walls 82, only one of which can be seen in FIG. 2. Condyler bearing surfaces 28, 30 are smooth and highly polished, generally spheroidally shaped and extend outwardly from external side walls 82, as is well known in the industry. Femoral component 22 further includes modular femoral stem 32 for insertion into femur 116 (FIGS. 3–5, 13, and 14), as is known in the art. Femoral component 22 further includes internal side walls 80, only one of which is illustrated in FIG. 2. Internal side walls 80 are substantially perpendicular to bearing box wall 76 and extend outwardly therefrom. Femoral component 22 is typically formed as a one-piece construction of an inert metal such as, e.g., a cobalt-chromium alloy.

Bearing box 70 is designed for placement between condyler bearing surfaces 28, 30 of femoral component 22 as illustrated, e.g., in FIG. 1. Bearing box 70 is further illustrated in FIGS. 10–12 and includes affixing protrusions 72, hinge pin aperture 62, hyperextension stop 66, and anti-rotation surface 78. As illustrated in FIG. 2, femoral component 22 includes affixing protrusion apertures 74 sized to receive affixing protrusions 72. FIG. 1 illustrates bearing box 70 operably positioned on femoral component 22, with anti-rotation surface 78 flush with bearing box wall 76 of femoral component 22, and affixing protrusions 72 received in affixing protrusion apertures 74. The abutting relationship of anti-rotation surface 78 with bearing box wall 76 discourages rotation of bearing box 70 about the longitudinal axis of affixing protrusions 72. When bearing box 70 is positioned on femoral component 22, hinge pin apertures 62 of bearing box 70 align with threaded hinge pin aperture 56 and hinge pin aperture 58 of femoral component 22. Bearing box 70 can be formed of any suitable plastic, such as, e.g., UHMWPE.

Hinge post 40 is rotatably connected to femoral component 22 via hinge pin 34. Hinge post 40 is placed between opposing walls of bearing box 70 and is positioned so that hinge pin aperture 52 is aligned with apertures 56, 58, and 62. The opposing walls of bearing box 70 thus act as a bearing surface between hinge post 40 and internal side walls 80 of femoral component 22. Prior to placement of hinge post 40 between opposing walls of bearing box 70, hinge pin sleeve 36 is operably positioned within hinge pin aperture 52 of hinge post 40. Hinge post 40 is formed from a cobalt-chromium alloy, while hinge pin sleeve 36 is formed from a suitable plastic, such as, e.g., UHMWPE. Hinge pin sleeve 36 acts as a bearing between hinge pin aperture 52 of hinge post 40 and hinge pin 34. Accordingly, hinge pin sleeve 36 includes hinge pin aperture 50 sized to accommodate hinge pin 34. After positioning hinge post 40 between the opposing walls of bearing box 70, hinge pin 34 is positioned through apertures 56, 62, 50, and 58. Hinge pin threads 60 are thereafter threadedly engaged in the threads of threaded hinge pin aperture 56 until the head of hinge pin 34 is flush with external side wall 82.

As illustrated in FIG. 1, hinge pin plug 120 is positioned within the hexagonal indentation of hinge pin 34 after installation of hinge pin 34 as described above. When positioned within the hexagonal indentation of hinge pin 34, hinge pin plug 120 is flush with the head of hinge pin 34. In use, hinge pin plug 120 substantially prohibits the entry of foreign materials into the hexagonal indentation of hinge pin 34. For example, hinge pin plug 120 substantially prohibits bone growth into the hexagonal indentation of hinge pin 34, as well as prohibiting positioning of bone cement therein. The above-described connection of hinge post 40 to femoral component 22 is performed prior to implantation of femoral component 22. Femoral component 22 is packaged and sold with bearing box 70, hinge post 40, hinge pin sleeve 36, hinge pin 34, and hinge pin plug 120 preassembled as described above, with the assembly preferably occurring in the manufacturing environment.

Pre-assembly of hinge post 40 to femoral component 22 eliminates a number of meticulous assembly steps (many of which were performed during implantation) which were required with constrained knees of the prior art. Furthermore, the assembly of hinge post 40 and femoral component 22 as described above facilitates replacement of various portions of knee prosthesis 20. Specifically, the threaded connection of hinge pin 34 to femoral component 22 allows for removal and replacement of various components of knee prosthesis 20 including, e.g., bearing box 70, hinge pin sleeve 36, and hinge post 40.

In use, femoral bone stock may abut external side walls 82 of femoral component 22 and extend to the underside of condyler bearing surfaces 28, 30. To remove hinge pin 34, a hole saw is utilized to remove a relatively small portion of femoral bone stock to provide access to hinge pin 34. Advantageously, femoral component 22 does not require extensive removal of femoral bone stock for implantation thereof (since bone stock can extend to the underside of condylar bearing surfaces 28, 30), and, furthermore, does not require removal of femoral component 22 to effect replacement of, e.g., hinge post 40, bearing box 70, or hinge pin sleeve 36. Upon accessing hinge pin 34 (e.g., utilizing a hole saw as described above), hinge pin plug 120 is removed, e.g., with a scalpel and forceps to provide access to the hexagonal indentation of hinge pin 34 so that a hexagonal wrench may be inserted therein to unthread hinge pin 34 from femoral component 22.

Knee prosthesis 20 includes a pair of hyperextension stop mechanisms. The first hyperextension stop comprises a portion of condylar bearing surfaces 28, 30 of increased radius of curvature as compared to the remaining condylar bearing surface. At three degrees of hyperextension this portion of increased radius of curvature will contact meniscal component 26 and act to retard further hyperextension. If hyperextension continues, the area of increased radius of curvature will cause femoral component 22 to lift away from meniscal component 26. The second hyperextension stop mechanism functions at four degrees of hyperextension to prohibit further hyperextension of knee prosthesis 20. The second hyperextension stop mechanism comprises hyperextension stop surface 66 of hinge post 40 and hyperextension stop 68 of bearing box 70. Hyperextension stop surface 66 comprises the concave back wall of cannulated hinge post 40 as illustrated, e.g., in FIGS. 2 and 3. Hyperextension stop 68 of bearing box 70 comprises a protrusion extending from the back wall of bearing box 70 opposite anti-rotation surface 78. Hyperextension stop 68 includes a convex outer surface as illustrated, e.g., in FIG. 12. Hyperextension stop surface 66 of hinge post 40 cooperates with hyperextension stop 68 of bearing box 70 to provide a hyperextension stop for knee prosthesis 20. Concave hyperextension stop surface 66 becomes flush with the convex outer surface of hyperextension stop 68 of bearing box 70 at four degrees of hyperextension to prevent further hyperextension of knee prosthesis 20.

Tibial component 24 is depicted in FIGS. 1–5, 8, 13, and 14. As illustrated, e.g., in FIG. 2, tibial component 24 includes tibial tray 98 connected to tibial stem 92. Stabilizing ribs 94 stabilize tibial tray 98 relative to tibial stem 92 and impede rotation of tibial component 24 in tibia 118 (see, e.g., FIG. 3). In one exemplary embodiment, tibial component 24 is formed from a cobalt-chromium alloy. Tibial component 24 further includes tibial bushing 64 positioned within hinge post extension aperture 110. Tibial bushing 64 is formed of plastic, such as, e.g., UHMWPE and provides a bearing surface between hinge post extension 42 and hinge post extension aperture 110 of tibial component 24. As described above, meniscal component 26 comprises a rotating bearing, and, thus, hinge post extension 42 will rotate relative to tibial component 24. Tibial bushing 64 facilitates this rotation of hinge post extension 42.

Tibial component 24 further includes rotation protrusion 96. As illustrated, e.g., in FIG. 3, rotation protrusion 96 protrudes upwardly from tibial tray 98 of tibial component 24 and further extends in a plane substantially parallel to tibial tray 98. Rotation protrusion 96 cooperates with cutout 90 of meniscal component 26 to guide rotation of meniscal component 26 about hinge post extension 42, as further described hereinbelow. FIGS. 31–36 illustrate an alternative embodiment tibial component 24b. As illustrated, e.g., in FIG. 35, tibial component 24b includes a pair of rotation protrusions, i.e., anterior rotation protrusion 180, and posterior rotation protrusion 182. Rotation protrusions 180, 182 protrude upwardly from tibial tray 98b of tibial component 24b and further extend in a plane substantially parallel to tibial tray 98b. Rotation protrusions 180, 182 cooperate with anterior cutout 160, and posterior cutout 162 of meniscal component 26b, respectively (see, e.g., FIGS. 21–26) to guide rotation of meniscal component 26b about the hinge post extension, as further described hereinbelow.

One embodiment of meniscal component 26 is illustrated in FIGS. 1–7, 13, and 14. Meniscal component 26 is formed from a suitable plastic such as, e.g., UHMWPE and provides a rotating bearing surface between femoral component 22 and tibial component 24. Meniscal component 26 includes bearing surfaces 86, 88 which contact condylar bearing surfaces 28, 30 of femoral component 22 during movement of knee prosthesis 20. As described above, meniscal component 26 further includes hinge post aperture 114 accommodating passage of hinge post 40 and, consequently, hinge post extension 42 therethrough. Meniscal component 26 is operable to rotate about the longitudinal axis of hinge post extension 42 to form a rotating bearing.

Meniscal components of varying heights may be constructed in accordance with the present invention. In one advantageous aspect of the present invention, meniscal component 26 is packaged for sale and use together with hinge post extension 42 to facilitate component choice and, in one embodiment, to ensure proper extension of hinge post extension 42 into tibial component 24. The extension of hinge post extension 42 into tibial component 24 functions to prevent separation of knee prosthesis 20 after implantation thereof. As is known in the art, the femoral component of a knee prosthesis may, in some situations, move relative to and away from the tibial component in a direction parallel to the longitudinal axis of the hinge post extension. With this in mind, hinge post extension 42 is made to be of sufficient length to be retained within tibial component 24 even in situations in which femoral component 22 moves as described immediately supra. In one exemplary embodiment, hinge post extension 42 extends four centimeters into hinge post extension aperture 110 in tibial component 24.

Meniscal component 26 includes cutout 90 which cooperates with rotation protrusion 96 of tibial component 24 to guide rotation of meniscal component 26 and to resist lifting of meniscal component 26 from tibial tray 98 of tibial component 24. As illustrated, e.g., in FIG. 3, cutout 90 accommodates the portion (i.e., lip) of rotation protrusion 96 extending in a plane substantially parallel to the plane containing tibial tray 98, with a portion (i.e., lip) of meniscal component 26 being positioned between rotation protrusion 96 and tibial tray 98 in a direction substantially perpendicular to the plane containing tibial tray 98. This configuration functions to discourage displacement of meniscal component 26 away from tibial tray 98 in a direction parallel to the longitudinal axis of hinge post extension 42. Furthermore, rotation protrusion 96 acts against the back of cutout 90 to limit rotation of meniscal component 26 about the longitudinal axis of hinge post extension 42.

Figure 22:
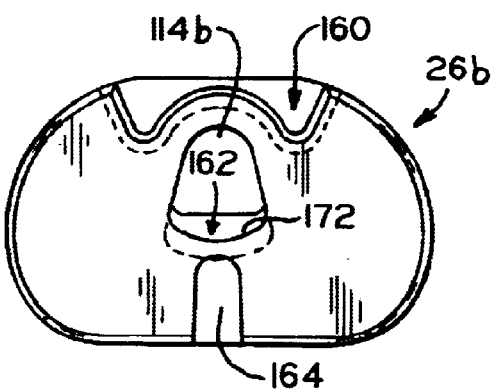
FIGS. 22, 23, 24, and 25 are bottom, back, front, and side elevational views thereof; respectfully.
Figure 23:
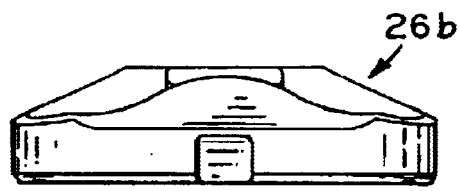
Figure 24:
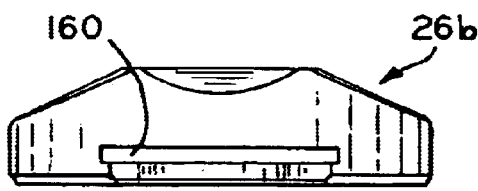
Figure 25:
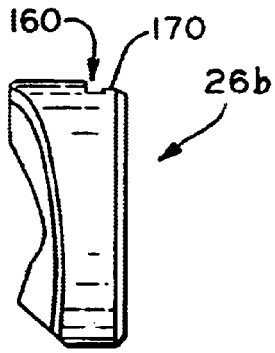
Figure 26:
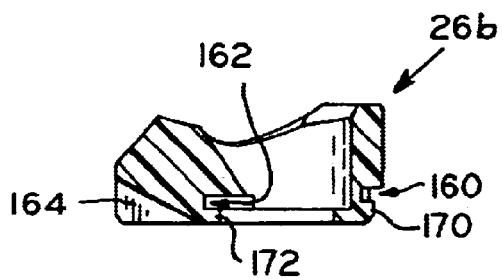
FIG. 26 is a sectional view thereof.

Meniscal component 26b illustrated in FIGS. 21–26, includes a pair of cutouts 160, 162 for cooperation with rotation protrusions 180, 182 of tibial component 24b (see, e.g., FIGS. 31–36) to guide rotation of meniscal component 26b and to resist lifting of meniscal component 26b from tibial tray 98b of tibial component 24b. As illustrated, e.g., in FIG. 26, meniscal component 26b includes anterior cutout 160 as well as posterior cutout 162, with anterior capture protrusion 170 and posterior capture protrusion 172 respectively extending therefrom. As illustrated in FIGS. 22 and 26, meniscal component 26b further includes channel 164 sized to accommodate posterior rotation protrusion 182 of tibial component 24b as will be further described hereinbelow.

As illustrated in FIGS. 27–30, tibial component 24b includes a pair of rotation protrusions, i.e., anterior rotation protrusion 180 and posterior rotation protrusion 182. As illustrated, e.g., in FIG. 30, anterior cutout 160 and posterior cutout 162 in meniscal component 26b respectively accommodate anterior capture protrusion 170 and posterior capture protrusion 172 formed in tibial component 26b. Specifically, cutouts 160, 162 accommodate the portion, i.e., lip of rotation protrusions 180, 182 extending in a plane substantially parallel to the plane containing tibial tray 98b, with a portion, i.e., lip of meniscal component 26b being positioned between the portions of rotation protrusions 180, 182 extending in a plane substantially parallel to the plane containing tibial tray 98b, and tibial tray 98b when meniscal component 26b is operably positioned atop tibial tray 98b as illustrated, e.g., in FIG. 30. The cooperation of rotation protrusions 180, 182 with capture protrusions 170, 172, as illustrated, e.g., in FIG. 30 functions to discourage displacement of meniscal component 26b away from tibial tray 98b in a direction perpendicular to tibial tray 98b when the knee prosthesis of the current invention is operably assembled as illustrated, e.g., in FIG. 1. Furthermore, cutouts 160, 162 are sized whereby rotation protrusions 180, 182 cooperate therewith to limit rotation of meniscal component 26b about an axis generally perpendicular to tibial tray 98b of tibial component 24b. In one exemplary embodiment, meniscal component 26b is capable of a total of sixty degrees of rotation from one extreme to the other.

Figure 27:
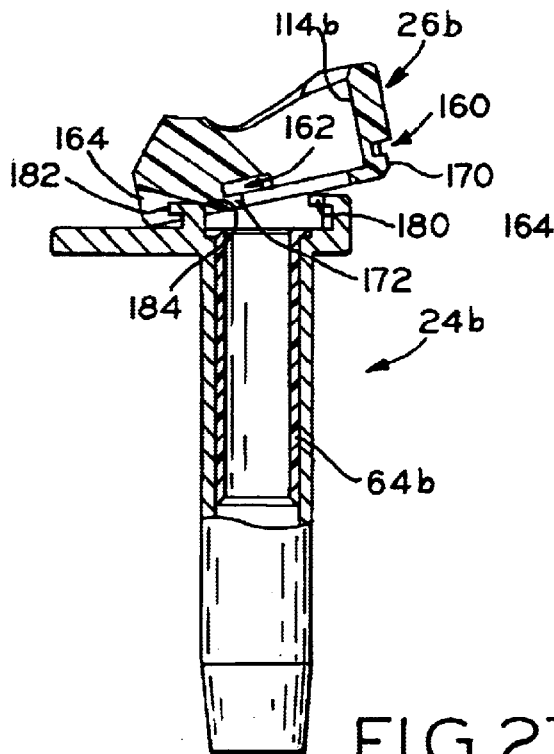
FIG. 27 is a sectional view illustrating initial placement of a meniscal component of the present invention on a tibial component of the present invention.
Figure 28:
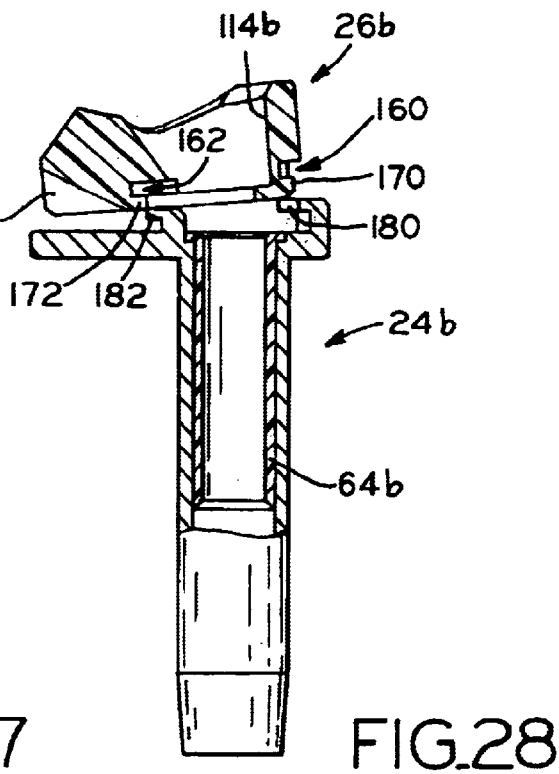
FIGS. 28–30 are sectional views progressively illustrating placement of a meniscal component of the present invention on a tibial component of the present invention, whereby the meniscal component is operable to rotate relative to the tibial component when operably positioned thereon, but is constrained from movement in an axial direction relative to the tibial stem, i.e., the meniscal component will not lift away from the tibial component.
Figure 29:
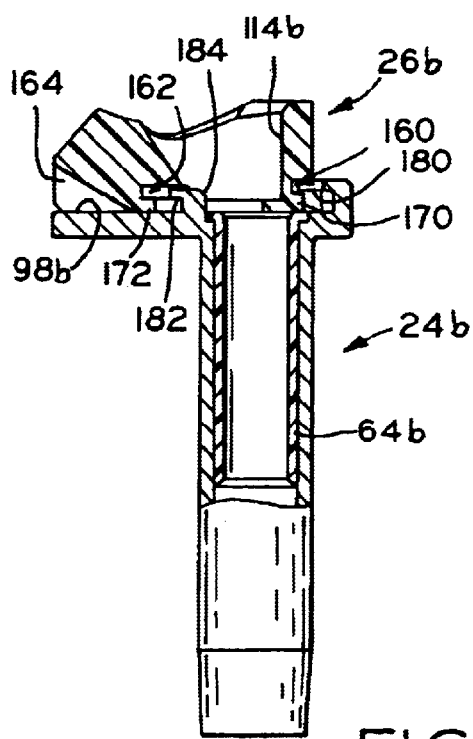
Figure 30:
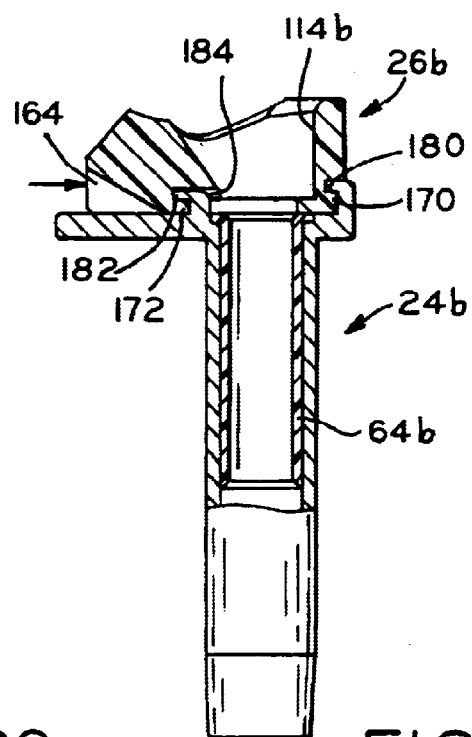
Figure 31:
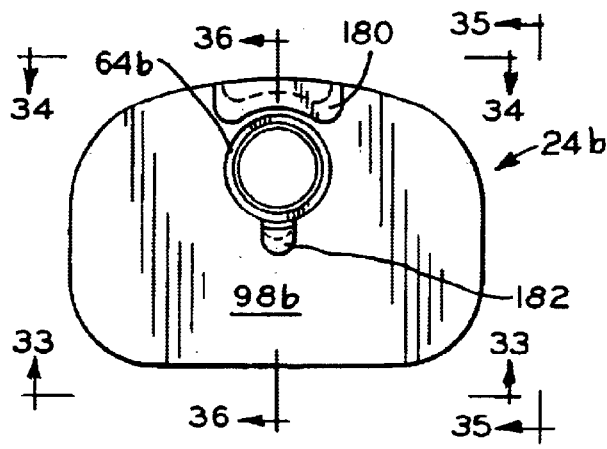
FIG. 31 is a top elevational view of a tibial component in accordance with the present invention.
Figure 32:
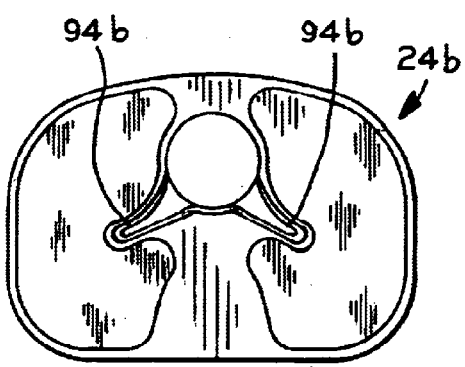
FIGS. 32, 33, 34, and 35 are bottom, back, front, and side elevational views thereof, respectively.
Figure 33:
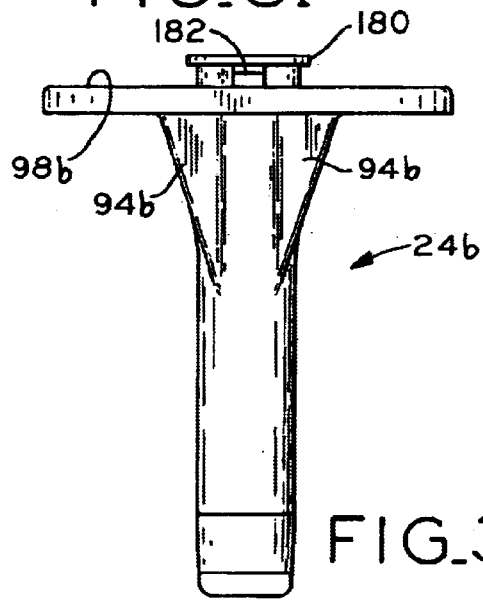
Figure 34:
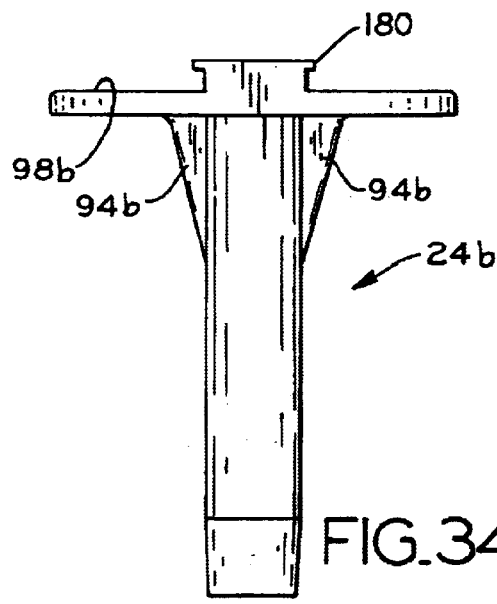
Figure 35:
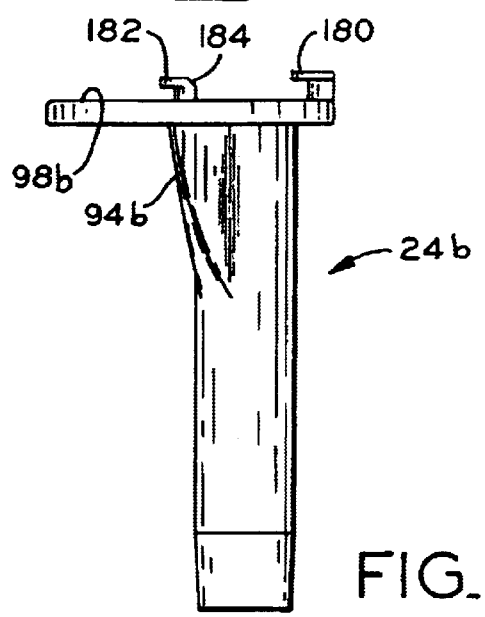
Figure 36:
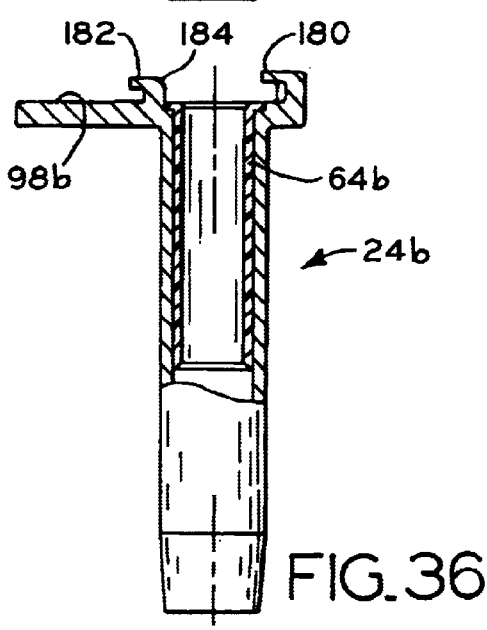
FIG. 36 is a sectional view thereof.

FIGS. 27–30 progressively illustrate movement of meniscal component 26b relative to tibial component 24b to achieve proper positioning of meniscal component 26b atop tibial tray 98b of meniscal component 24b. As illustrated in FIG. 27, posterior rotation protrusion 182 of tibial component 24b is positioned within channel 164 formed in meniscal component 26b, with meniscal component 26b resting atop rotation protrusion 180. Meniscal component 26b is thereafter moved posteriorly as illustrated in FIG. 28 until capture protrusions 170, 172 no longer rest atop rotation protrusions 180, 182, and meniscal component 26b is moved into contact with tibial tray 98b as illustrated in FIG. 29. Meniscal component 26b is subsequently moved anteriorly so that capture protrusions 170, 172 engage rotation protrusions 180, 182, respectively, to prevent movement of meniscal component 26b in a direction generally perpendicular to the plane containing tibial tray 98b, as illustrated in FIG. 30. As illustrated in FIG. 27, posterior rotation protrusion 82 includes bevel 184 to facilitate posterior movement of meniscal component 26b. Once meniscal component 26b is moved into the position illustrated in FIG. 30, hinge post extension 42 may be operably positioned within the tibial component as illustrated, e.g., in FIG. 4.

Figure 5:
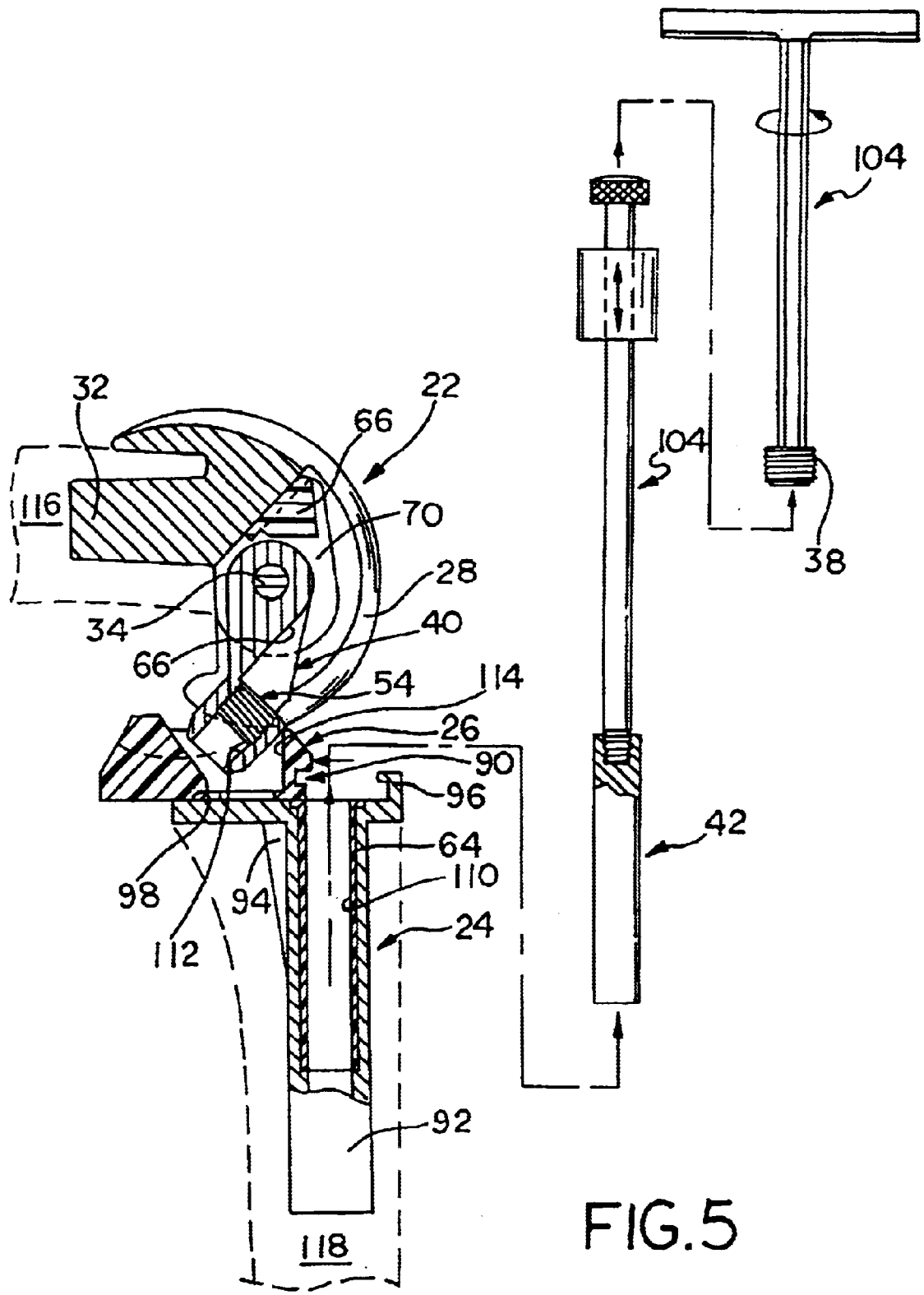
FIG. 5 is a cutaway, exploded view illustrating removal of the hinge post extension.
Figure 21:
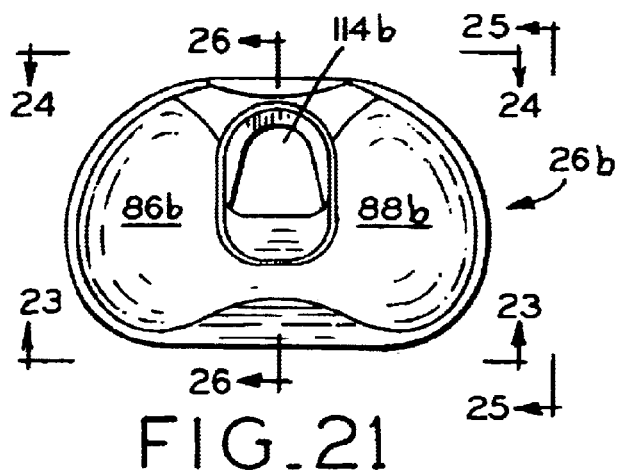
FIG. 21 is a top elevational view of a meniscal component in accordance with the present invention.

Positioning of meniscal component 26b as described above in conjunction with FIGS. 27–30, may be effected in vivo with femoral component 22 in place, i.e., implanted in femur 116 as illustrated e.g., in FIG. 5. If meniscal component 26b is positioned with femoral component 22 in place, the steps described above will occur with condylar bearing surfaces 28, 30 resting atop bearing surfaces 86b, 88b (FIG. 21) of meniscal component 26b, and with hinge post 40 positioned within hinge post aperture 114b of meniscal component 26b. As meniscal component 26b is moved relative to tibial component 24b as illustrated in FIGS. 27–30, hinge post 40 will rotate relative to femoral component 22 and move with meniscal component 26b.

As illustrated in FIG. 5, meniscal component 26 may be slid out from between tibial component 24 and femoral component 22 when hinge post extension 42 has been removed from knee prosthesis 20. As illustrated, hinge post aperture 114 is sized to allow rotation of hinge post 40 so that meniscal component 26 may be slid out from its position between femoral component 22 and tibial component 24. Similarly, meniscal component 26b may be removed from position between tibial component 24b and the femoral component when hinge post extension 42 has been removed from knee prosthesis 20. If meniscal component 26b and tibial component 24b are utilized, meniscal component 26b is removed by reversing the steps utilized to position meniscal component 26b atop tibial component 24b described above in conjunction with FIGS. 27–30. This allows for replacement of an implanted meniscal component 26 without requiring removal of hinge post 40.

FIG. 5 illustrates removal of hinge post extension 42 to accommodate replacement of meniscal component 26. As illustrated, hinge plug wrench 102 engages hinge plug 38 for removal thereof. After removal of hinge plug 38, slap hammer 104 is threadedly engaged with threaded aperture 44 in hinge post extension 42. Slap hammer 104 may then be utilized to unlock the engagement of locking taper 46 in elongate hinge post extension aperture 112 so that hinge post extension 42 may be removed. If hinge post extension 42b illustrated in FIG. 2a is utilized, wrench 102 will be utilized to rotate hinge post extension 42b to cause threaded proximal end 150 thereof to retreat from hinge plug threads 54 in hinge post 40, thereby releasing engagement of locking taper 46b in elongate hinge post extension aperture 112 and allowing for removal of hinge post extension 42b.

FIGS. 13 and 14 illustrate a further alternative embodiment of the knee prosthesis of the current invention. This alternative embodiment utilizes hinge post extension 42a having locking taper 46a, cylindrical extension 48a, and flange 106. In this embodiment, a locking instrument may be utilized to apply force atop hinge post extension 42a so that locking taper 46a is seated in elongate hinge post extension aperture 112 and locked therein. Flange 106 may be utilized to facilitate removal of hinge post extension 42a. As illustrated in FIG. 13, set screw 108 may be utilized as a secondary lock for hinge post extension 42a.

FIGS. 15, 16 and 17 illustrate another alternative embodiment of the hinge post extension and tibial bushing of the present invention. In this embodiment, tibial component 24a includes annular tibial bushing expansion groove 122 formed in hinge post extension aperture 110. Tibial bushing 64a includes retaining flange 130 positioned within annular tibial bushing expansion groove 122. FIG. 15 illustrates insertion of cylindrical extension 48b of the hinge post extension into tibial bushing 64a positioned within tibial component 24a. As cylindrical extension 48b proceeds into tibial bushing 64a, bevel 126 contacts annular locking protrusion 128 of tibial bushing 64a and causes outward movement of retaining flange 130 as illustrated in FIG. 16 to allow cylindrical extension 48b to proceed to its seated position as illustrated in FIG. 17. Annular tibial bushing expansion groove 122 is sized to allow radial expansion of retaining flange 130 to accommodate placement of cylindrical extension 48b within tibial bushing 64a. In the fully seated position (FIG. 17) cylindrical extension 48b is locked in place by the engagement of annular locking protrusion 128 in annular locking groove 124. Furthermore, retaining flange 130 cooperates with annular tibial bushing expansion groove 122 to prohibit axial displacement of tibial bushing 64a and, consequently, cylindrical extension 48b. In this embodiment, the femoral component is retained in abutting relationship to the meniscal component and lift off of the femoral component is substantially prohibited. Tibial bushing 64a is, in one exemplary embodiment, formed of UHMWPE.

FIGS. 18 and 19 illustrate yet another alternative embodiment of the knee prosthesis of the current invention. In this embodiment, locking clip 134 is utilized to retain the position of hinge post 40b within hinge post aperture 114 of meniscal component 26a. Hinge post 40b is rotatably attached to femoral component 22 utilizing hinge pin 34 as described above. In this embodiment, hinge post 40b includes locking clip grooves 132, and meniscal component 26a includes locking clip apertures 136. Upon positioning of hinge post 40b within hinge post aperture 114, locking clip 134 is positioned as illustrated in FIG. 19 with the prongs of locking clip 134 being inserted into locking clip apertures 136 of meniscal component 26a. As illustrated in FIG. 19, locking clip 134 engages locking clip grooves 132 to retain hinge post 40b within hinge post aperture 114 of meniscal component 26a. In this embodiment, lift off of femoral component 22 is prohibited by the engagement of hinge post 40b with meniscal component 26a. This embodiment of the knee prosthesis of the current invention may further utilize a meniscal component cutout together with a rotation protrusion on the tibial component to resist lifting of the meniscal component from the tibial tray as described above.

FIG. 20 illustrates a further alternative embodiment of the hinge post of the present invention. Hinge post 40c illustrated in FIG. 20 includes reinforcing material 138 to strengthen hinge post 40c.

While this invention has been described as a prosthetic knee with a rotating bearing, it is contemplated that various aspects of the present invention, including, e.g., the cannulated hinge post will be utilized with a prosthetic knee having a fixed bearing.

While this invention has been described as having exemplary designs, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A prosthetic knee, comprising:
   a femoral component including a condylar bearing surface;
   a meniscal component including a cooperative bearing surface facing said condylar bearing surface of said femoral component; and
   a tibial component including guide means for guiding rotation of said meniscal component about an axis substantially perpendicular to a tibial tray of said tibial component, said guide means further for preventing substantial lift off of said meniscal component away from said tibial component.

2. The prosthetic knee of claim 1, wherein said femoral component includes a hinge post rotatably connected thereto, said hinge post including an elongate hinge post extension aperture sized for placement of a hinge post extension therein, whereby said hinge post extension traverses a first end of said hinge post extension aperture and protrudes from a second end of said hinge post extension aperture when operably positioned therein, said first end and said second end of said hinge post extension aperture comprising opposing ends of said elongate hinge post extension aperture, said tibial component including a second hinge post extension aperture, whereby said hinge post extension is positioned within said second hinge post extension aperture when the prosthetic knee is operably assembled, said meniscal component including a hinge post aperture, whereby said hinge post is positioned within said hinge post aperture when the prosthetic knee is operably assembled.

3. The prosthetic knee of claim 1, wherein said guide means limits rotation of said meniscal component about said axis to a total of 60° of rotation.

4. A prosthetic knee, comprising:
   a femoral component including a condylar bearing surface;
   a meniscal component including a cooperative bearing surface facing said condylar bearing surface of said femoral component; and
   a tibial component including a rotation protrusion cooperating with a cutout of said meniscal component to guide rotation of said meniscal component about an axis substantially perpendicular to a tibial tray of said tibial component, said rotation protrusion including a lip extending substantially parallel to said tibial tray of said tibial component, said rotation protrusion lip facing an opposing lip formed in said cutout in said meniscal component, said meniscal component lip being positioned between said tibial tray and said rotation protrusion lip.

5. The prosthetic knee of claim 4, wherein said femoral component includes a hinge post rotatably connected thereto, said hinge post including an elongate hinge post extension aperture sized for placement of a hinge post extension therein, whereby said hinge post extension traverses a first end of said hinge post extension aperture and protrudes from a second end of said hinge post extension aperture when operably positioned therein, said first end and said second end of said hinge post extension aperture comprising opposing ends of said elongate hinge post extension aperture, said tibial component including a second hinge post extension aperture, whereby said hinge post extension is positioned within said second hinge post extension aperture when the prosthetic knee is operably assembled, said meniscal component including a hinge post aperture, whereby said hinge post is positioned within said hinge post aperture when the prosthetic knee is operably assembled.

6. The prosthetic knee of claim 4, cutout in said meniscal component is sized whereby said rotation protrusion cooperates with said cutout, to limit rotation of said meniscal component about said axis to a total of 60° of rotation.

7. A prosthetic knee, comprising:
   a femoral component including a condylar bearing surface;
   a meniscal component including a cooperative bearing surface facing said condylar bearing surface of said femoral component; and
   a tibial component including a rotation protrusion positioned in a cutout of said meniscal component, said rotation protrusion including a lip extending substantially parallel to a tibial tray of said tibial component, said rotation protrusion lip facing an opposing lip formed in said cutout in said meniscal component, said meniscal component lip being positioned between said tibial tray and said rotation protrusion lip, said rotation protrusion moveable within said cutout of said meniscal component.

8. The prosthetic knee of claim 7, wherein said femoral component includes a hinge post rotatably connected thereto, said hinge post including an elongate hinge post extension aperture sized for placement of a hinge post extension therein, whereby said hinge post extension traverses a first end of said hinge post extension aperture and protrudes from a second end of said hinge post extension aperture when operably positioned therein, said first end and said second end of said hinge post extension aperture comprising opposing ends of said elongate hinge post extension aperture, said tibial component including a second hinge post extension aperture, whereby said hinge post extension is positioned within said second hinge post extension aperture when the prosthetic knee is operably assembled, said meniscal component including a hinge post aperture, whereby said hinge post is positioned within said hinge post aperture when the prosthetic knee is operably assembled.

9. The prosthetic knee of claim 7, wherein said cutout in said meniscal component is sized whereby said rotation protrusion cooperates with said cutout, to limit rotation of said meniscal component about an axis substantially perpendicular to said tibial tray to a total of 60° of rotation.

10. A prosthetic knee, comprising:
    a femoral component having a hinge post rotatably connected thereto, said hinge post including an elongate hinge post extension aperture sized for placement of a hinge post extension therein, whereby said hinge post extension traverses a first end of said hinge post extension aperture and protrudes from a second end of said hinge post extension aperture when operably positioned therein, said first and said second ends of said hinge post extension aperture comprising opposing ends of said elongate hinge post extension aperture, said first end of said hinge post extension aperture having threads cooperating with a threaded proximal end of said hinge post extension to connect said hinge post extension to said hinge post; and
    a tibial component including a second hinge post extension aperture, whereby said hinge post extension is positioned within said second hinge post extension aperture when the prosthetic knee is operably assembled.

11. The prosthetic knee of claim 10, further comprising:
a meniscal component positioned between said femoral component and said tibial component, said femoral component including a condylar bearing surface, said meniscal component including a cooperative bearing surface facing said condylar bearing surface of said femoral component, said meniscal component including a hinge post aperture, whereby said hinge post is positioned within said hinge post aperture when the prosthetic knee is operably assembled.

12. The prosthetic knee of claim 11, wherein said tibial component includes a rotation protrusion cooperating with a cutout of said meniscal component to guide rotation of said meniscal component about a longitudinal axis of said hinge post extension.

13. The prosthetic knee of claim 10, wherein said rotation protrusion includes a lip extending substantially parallel to a tibial tray of said tibial component, said rotation protrusion lip facing an opposing lip formed in said cutout of said meniscal component, said meniscal component lip being positioned between said tibial tray and said rotation protrusion lip.

14. The prosthetic knee of claim 11, wherein said condylar bearing surface includes a first portion and a second portion, said first portion having a first radius of curvature, said second portion having a second radius of curvature, whereby an axis of rotation of said femoral component remains constant during flexion and extension of the prosthetic knee when said first portion contacts said cooperative bearing surface of said meniscal component, whereby said axis of rotation of said femoral component moves away from said meniscal component when said second portion of said femoral component contacts said cooperative bearing surface of said meniscal component, whereby said second portion of said femoral component contacts said meniscal component at three degrees of hyperextension of the prosthetic knee.

15. The prosthetic knee of claim 10, further comprising:
a bearing box connected to said femoral component, said bearing box interposed between said hinge post and said femoral component, whereby said hinge post will not contact said femoral component during flexion and extension of the prosthetic knee, said bearing box including a hyperextension stop, said hinge post including a hyperextension stop surface, said hyperextension stop contacting said hyperextension stop surface to prevent further hyperextension of the prosthetic knee beyond a predetermined point of hyperextension.

16. The prosthetic knee of claim 15, wherein said hyperextension stop comprises a convex protrusion.

17. The prosthetic knee of claim 15, wherein said hyperextension stop surface comprises a concave portion of said elongate hinge post extension aperture.

18. The prosthetic knee of claim 15, wherein said predetermined point of hyperextension comprises four degrees of hyperextension of the prosthetic knee.

19. The prosthetic knee of claim 10, wherein said hinge post extension includes a threaded aperture.

20. A prosthetic knee, comprising:
a femoral component including a condylar bearing surface;
a meniscal component including a cooperative bearing surface facing said condylar bearing surface of said femoral component; and
a tibial component including an anterior rotation protrusion, and a posterior rotation protrusion cooperating with an anterior cutout and a posterior cutout of said meniscal component, respectively, to guide rotation of said meniscal component about an axis substantially perpendicular to a tibial tray of said tibial component, said anterior rotation protrusion including an anterior lip extending substantially parallel to said tibial tray of said tibial component, said posterior rotation protrusion including a posterior lip extending substantially parallel to said tibial tray of said tibial component, said anterior rotation protrusion lip facing an anterior opposing lip formed in said anterior cutout of said meniscal component, said anterior meniscal component lip being positioned between said tibial tray and said anterior rotation protrusion lip, said posterior rotation protrusion lip facing a posterior opposing lip formed in said posterior cutout of said meniscal component, said posterior meniscal component lip being positioned between said tibial tray and said posterior rotation protrusion lip.

21. The prosthetic knee of claim 20, wherein said femoral component includes a hinge post rotatably connected thereto, said hinge post including an elongate hinge post extension aperture sized for placement of a hinge post extension therein, whereby said hinge post extension traverses a first end of said hinge post extension aperture and protrudes from a second end of said hinge post extension aperture when operably positioned therein, said first end and said second end of said hinge post extension aperture comprising opposing ends of said elongate hinge post extension aperture, said tibial component including a second hinge post extension aperture, whereby said hinge post extension is positioned within said second hinge post extension aperture when the prosthetic knee is operably assembled, said meniscal component including a hinge post aperture, whereby said hinge post is positioned within said hinge post aperture when the prosthetic knee is operably assembled.

22. The prosthetic knee of claim 20, wherein said anterior cutout in said meniscal component and said posterior cutout in said meniscal component are both sized whereby said anterior rotation protrusion and said posterior rotation protrusion cooperate with said anterior cutout and said posterior cutout, respectively, to limit rotation of said meniscal component about said axis substantially perpendicular to said tibial tray to a total of 60° of rotation.

23. A prosthetic knee, comprising:
a femoral component including a condylar bearing surface;
a meniscal component including a cooperative bearing surface facing said condylar bearing surface of said femoral component; and
a tibial component including an anterior rotation protrusion, and a posterior rotation protrusion positioned in an anterior cutout and a posterior cutout of said meniscal component, respectively, said anterior rotation protrusion including an anterior lip extending substantially parallel to a tibial tray of said tibial component, said posterior rotation protrusion including a posterior lip extending substantially parallel to said tibial tray of said tibial component, said anterior rotation protrusion lip facing an anterior opposing lip formed in said anterior cutout of said meniscal component, said anterior meniscal component lip being positioned between said tibial tray and said anterior rotation protrusion lip, said posterior rotation protrusion lip facing a posterior opposing lip formed in said posterior cutout of said meniscal component, said posterior meniscal component lip being positioned between said tibial tray and said posterior rotation protrusion lip, said anterior rotation protrusion moveable within said anterior cutout of said meniscal component, said posterior rotation protrusion moveable within said posterior cutout of said meniscal component.

24. The prosthetic knee of claim 23, wherein said femoral component includes a hinge post rotatably connected thereto, said hinge post including an elongate hinge post extension aperture sized for placement of a hinge post extension therein, whereby said hinge post extension traverses a first end of said hinge post extension aperture and protrudes from a second end of said hinge post extension aperture when operably positioned therein, said first end and said second end of said hinge post extension aperture comprising opposing ends of said elongate hinge post extension aperture, said tibial component including a second hinge post extension aperture, whereby said hinge post extension is positioned within said second hinge post extension aperture when the prosthetic knee is operably assembled, said meniscal component including a hinge post aperture, whereby said hinge post is positioned within said hinge post aperture when the prosthetic knee is operably assembled.

25. The prosthetic knee of claim 23, wherein said anterior cutout in said meniscal component and said posterior cutout in said meniscal component are both sized whereby said anterior rotation protrusion and said posterior rotation protrusion cooperate with said anterior cutout and said posterior cutout, respectively, to limit rotation of said meniscal component about an axis substantially perpendicular to said tibial tray to a total of 60° of rotation.

* * * * *